(12) United States Patent
Kogut et al.

(10) Patent No.: US 6,221,348 B1
(45) Date of Patent: Apr. 24, 2001

(54) IMMUNE LYMPHOKINE-MEDIATED CONTROL OF SALMONELLOSIS IN SWINE

(75) Inventors: Michael H. Kogut; Kenneth J. Genovese; Larry H. Stanker, all of College Station, TX (US)

(73) Assignees: The United States of America as represented by the Secretary of Agriculture, Washington, DC (US); The Texas A&M University System, College Station, TX (US)

( * ) Notice: Subject to any disclaimer, the term of this patent is extended or adjusted under 35 U.S.C. 154(b) by 0 days.

(21) Appl. No.: 09/160,084

(22) Filed: Sep. 24, 1998

(51) Int. Cl.$^7$ .................. A61K 45/00; A61K 47/00; A23K 1/165; A23K 1/17; A01N 37/18
(52) U.S. Cl. .................. 424/85.1; 424/85.2; 424/439; 424/442; 514/2
(58) Field of Search .................. 424/85.1, 85.2, 424/439, 442; 435/325, 375; 514/2, 8, 885

(56) References Cited

U.S. PATENT DOCUMENTS

| | | | |
|---|---|---|---|
| 5,034,513 | 7/1991 | Frederickson et al. | 530/351 |
| 5,691,200 | 11/1997 | Kogut et al. | 435/349 |
| 5,698,193 | 12/1997 | Kogut et al. | 424/85.1 |

OTHER PUBLICATIONS

Scholl et al., "Virus–specific cellular blastogenesis and itnerleukin–2 production in swine after recovery from African swine fever", *Am J Vet Res*, vol. 50, No. 10, Oct. 1989, pp. 1781–1786.

Federspiel, Genevieve, et al., "Analyses of the primary in vitro responsiveness of non–immune porcine peripheral blood mononuclear cells with reference to immunization by African swine fever virus antigen and treatment with leucine methyl ester", *Immunology Letters*, 34, 1992, pp. 161–172.

Dillender, Margaret J., et al., "Characteristics of T lymphocyte cell lines established from NIH minipigs challenge inoculated with *Trichinella spirallis*", *Veterinary Immunology and Immunopathology*, 35, 1993, pp. 301–319.

Davies PR et. al., "Isolation of Salmonella Serotypes from Feces of Pigs Raised in a Multiple–Site Production System." J. Am. Vet. Med. Assoc., vol. 212, No. 12, pp. 1925–1929, Jun. 15, 1998.*

* cited by examiner

Primary Examiner—Gary L. Kunz
Assistant Examiner—Robert S. Landsman
(74) Attorney, Agent, or Firm—M. Howard Silverstein; Randall E. Deck; John D. Fado

(57) ABSTRACT

A method and composition for treating swine to increase their resistance to pathogenic microorganisms are disclosed. Microbial infections may be prevented or reduced in swine populations by administration of immune lymphokines which have been produced by the splenic T cells of immunized swine. The process and compositions are particularly useful for the control of Salmonella in swine.

11 Claims, 3 Drawing Sheets

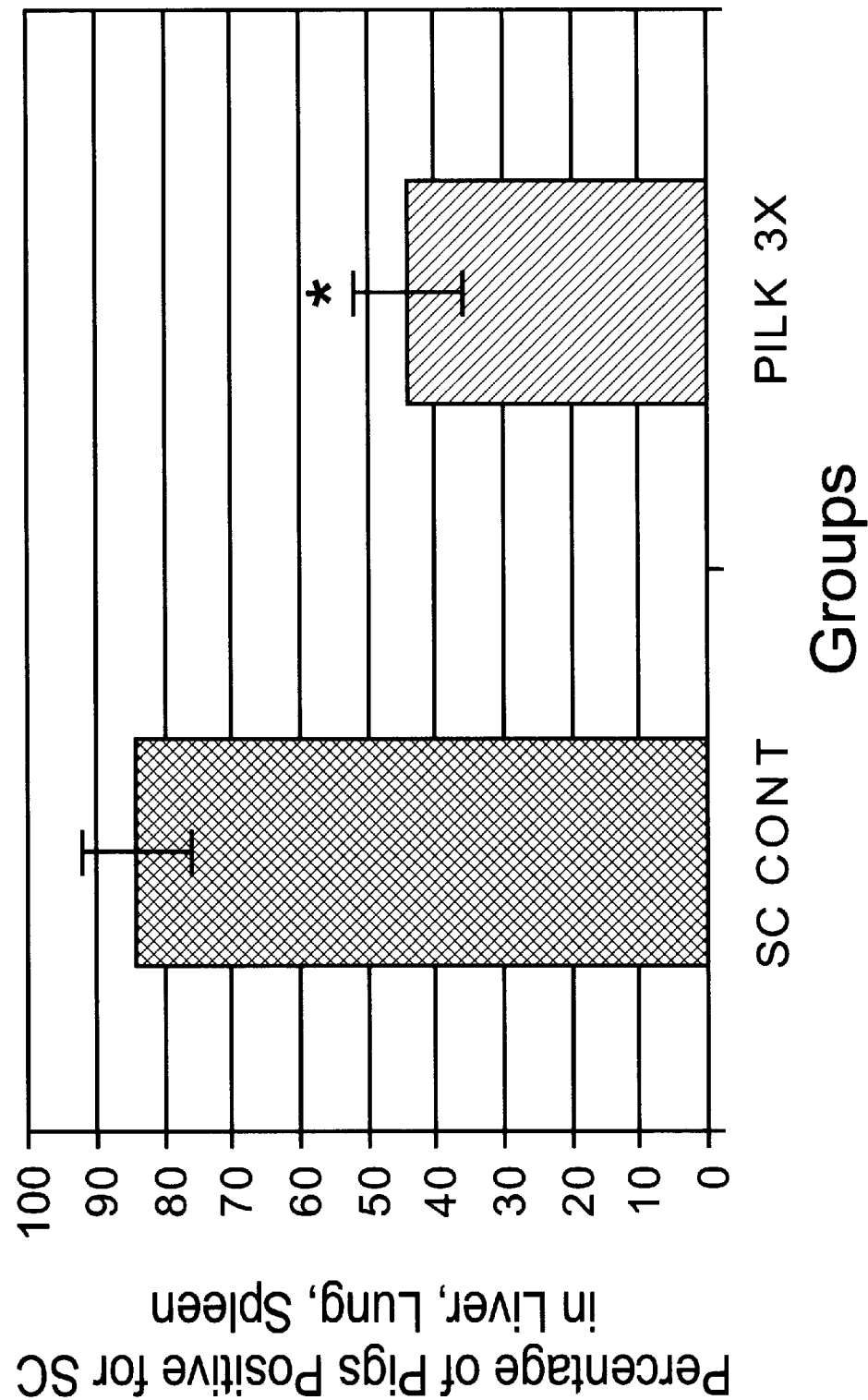

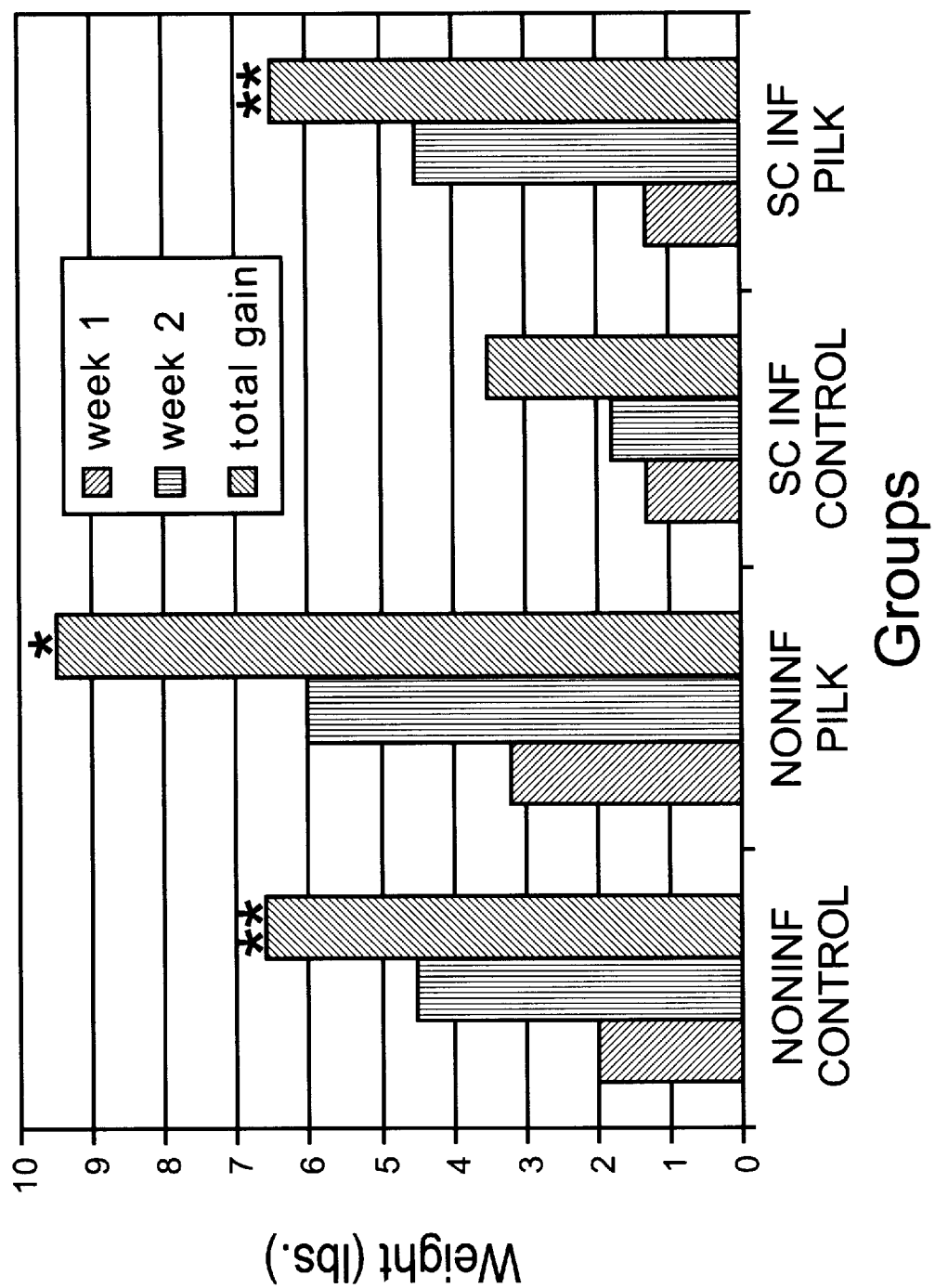

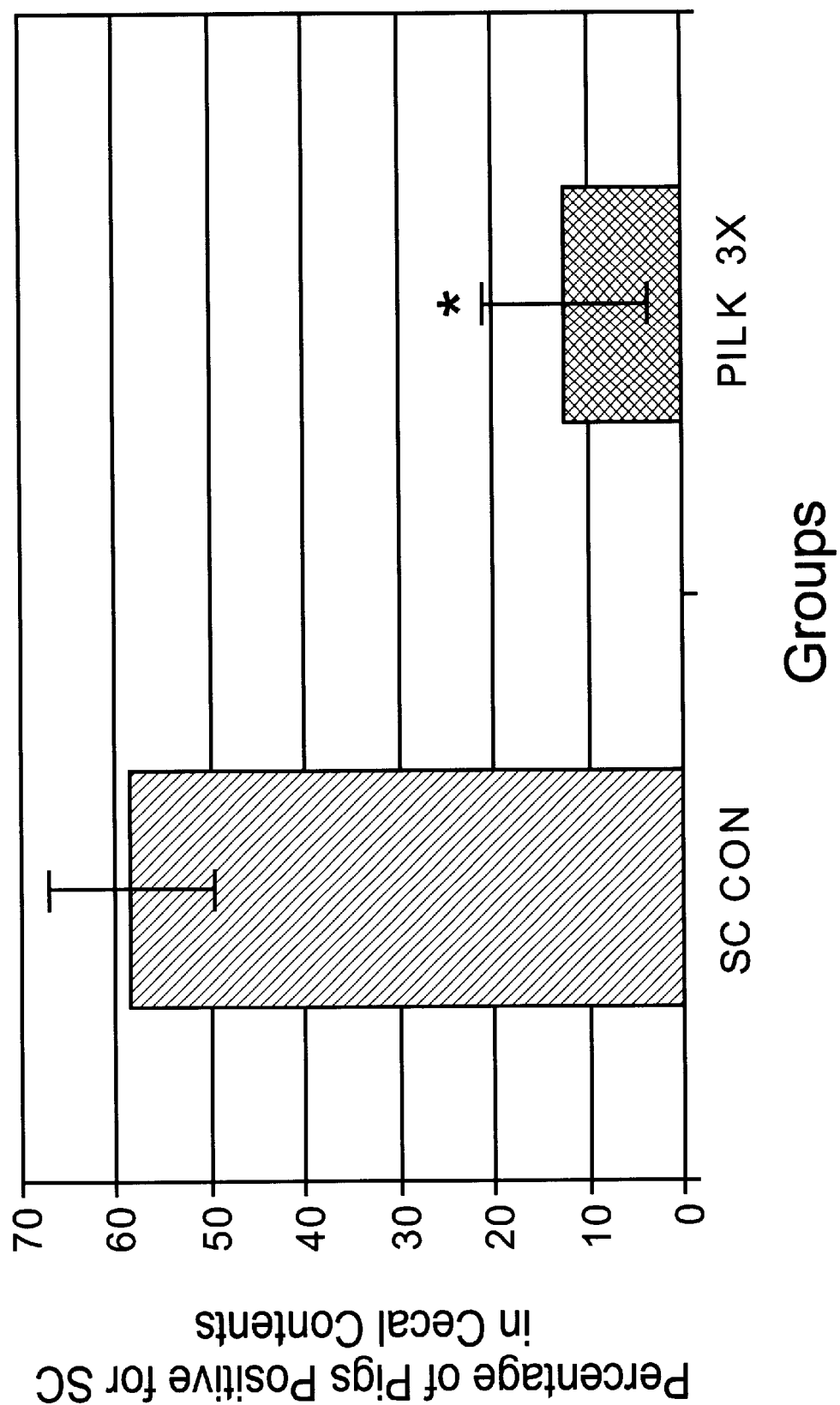

IMMUNE LYMPHOKINE-MEDIATED CONTROL OF SALMONELLOSIS IN SWINE

BACKGROUND OF THE INVENTION

1. Field of the Invention

This invention relates to the production of immune lymphokines and the use of those lymphokines to combat microbial infections.

2. Description of the Prior Art

Despite the efforts of researchers and public health agencies, the incidence of human salmonellosis has increased over the past 20 years. The number of actual reported cases of human Salmonella infection exceeds 40,000 per year. However, the Communicable Disease Center estimates that the true incidence of human Salmonella infections in the U.S. each year may be as high as 2 to 4 million. Animal food products, including swine, remain a significant source of human infection.

In addition to the impact of Salmonella on human health, Salmonella infections in swine cost the United States swine industry more than 100 million dollars annually (Schwartz, 1990, "Salmonellosis in Midwestern Swine", In: Proceedings of the United States Animal Health Assoc., pp. 443–449). In the U.S., salmonellosis caused by *S. choleraesuis*, the etiologic agent of swine paratyphoid, occurs most frequently. While pigs can be exposed to a broad host range of salmonellae, such as *S. typhimurium*, from a variety of sources, *S. choleraesuis* is a host adapted pathogen rarely isolated from non-swine sources (Schwartz, ibid). Thus, natural infection of new animals by *S. choleraesuis* occurs primarily via horizontal transmission from infected animals which shed the pathogens from their gastrointestinal tract.

Blecha et al. (1983, J. Anim. Sci., 56:396–400) and Wilcock and Schwartz [Salmonellosis, IN: *Diseases of Swine*, 7th edition, Leman et al. (eds.), Iowa State University Press, Ames, Iowa, 1992, pp. 570–583] have disclosed that weaned pigs have an increased susceptibility to infectious diseases in comparison to mature and suckling swine. This increase in susceptibility to infectious agents post-weaning may be comprised of multiple factors, including loss of maternally derived antibodies, developmental deficiencies of the immune response, and stress-induced susceptibility due to increased glucocorticoids in these pigs [Blecha et al. (ibid); Wilcock and Schwartz (ibid); Blecha et al. (1985, Am. J. Vet. Res., 46:1934–1937); Aurich et al. (1990, J. Reprod. Fert., 89:605–612); Abughali et al. (1994, Blood, 83:1086–1092); and El-Awar and Hahn (1991, J. Leuk. Biol., 49:227–235].

With the trend leaning towards weaning piglets from sows earlier, 8–10 days of age in some cases, the influence of developmental deficiencies of the immune system on increased susceptibility to infectious diseases becomes an even more important concern (Blecha et al., ibid). Developmental deficiencies in immune functions and subsequent susceptibility to infectious diseases have been well documented in neonatal mammalian species. Human, equine and bovine neonates exhibit deficient or impaired neutrophil and T cell functions for the first weeks of life [Coignal et al. (1984, Am. J. Vet. Res., 45:898–901); Hauser et al. (1986, Am. J. Vet. Res., 47:152–153); Hill (1997, Pediatric Research, 22:375–382); Miller (1979, Pediatrics (suppl.), 709–712); Rosenthal and Cairo (1995, Intern. J. Ped. Hem./ Onc., 2:477–487); Higuchi et al. (1997, J. Vet. Med. Sci., 59:271–276); Lee and Roth (1992, Comp. Haem. Intern., 2:140–147); Lee and Kehrli (Am. J. Vet. Res., 59:37–43); and Zwahlen et al. (1992, J. Leuk. Biol., 51:264–269)]. Susceptibility to gram negative bacteria has also been well documented in equine, porcine, and bovine neonates [Carter and Martens (1986, Comp. Cont. Educ. Pract. Vet., 8:S256–S270); Drieson et al. (1993, Aust. Vet. J., 70:259–262); and Selim et al. (1995, Vaccine, 13:381–390)]. Young pigs exhibit developmental deficiencies within both the humoral and cellular arms of the immune system. Development of B and T cell compartments in neonatal pigs takes several weeks to become stable and the different classes of immunoglobulins in various sites change with the age of the pig [Bianchi et al. (1992, Vet. Immun. Immunopath., 33:201–222) and McCauley and Hartmann (1984, Res. Vet. Sci., 37:234–241)]. Decreased mitogenic responses of T cells and decreased neutrophil function from young pigs have also been observed [Blecha et al. (1983, ibid); El-Awar and Hahn (ibid); Shi et al. (1994, J. Leuk. Biol., 56:88–94); and Hoskinson et al. (1990, J. Anim. Sci., 68:2471–2478)].

Considering the widespread presence of Salmonella in the environment, it is unlikely that animals can be completely protected from Salmonella exposure. Therefore, researchers have continued to investigate means of increasing resistance to colonization in animals exposed to Salmonella. Studies have focused on the evaluation of vaccines, establishment of protective normal intestinal flora, and the identification of feed additives that will inhibit Salmonella growth and colonization. The role of host immunity against Salmonella colonization is unclear, and it also remains uncertain if stimulation of immune responses will effectively enhance colonization resistance. Experimental vaccines have not proven to be consistently effective.

Our laboratory has previously focused on developmental deficiencies of the immune response of neonatal avian species during the first 4-to-7 days post-hatch and the possibility of augmenting the immune response during the first week post-hatch and at other times of increased susceptibility to disease. Accompanying these deficiencies in immune functions is an increased susceptibility to bacterial infections [Ziprin et al. (1989, Poult. Sci., 68:1637–1642)].

We have demonstrated that the administration of immune lymphokines (ILK) derived from the splenic T cells of *Salmonella enteritidis* (SE)-immune chickens protects both chickens and turkeys from SE organ invasion at one day-of-age [McGruder et al. (1993, Poult. Sci., 72:2264–2271); Ziprin et al. (1996, Avian Dis., 40:186–192); and Tellez et al. (1993, Avian Dis., 37:1062–1070)]. Further, heterophils isolated from the peripheral blood of day-old chickens and turkeys treated with ILK exhibit increased functional capabilities, showing increased phagocytic and bactericidal activities [Lowry et al. (ibid); and Kogut et al. (1995, J. Leuk. Biol., 57:56–62)]. These early studies utilizing ILK involved the batchwise production of SEILK from hyperimmunized chickens for continued experimental use. More recently, Kogut et al. (U.S. patent application Ser. No. 08/929,074, and U.S. Pat. No. 5,691,200) described the production of immortalized cell lines from avian T lymphocytes and the use of those cell lines to produce the SEILK.

SUMMARY OF THE INVENTION

We have now discovered a method and compositions for treating swine to increase their resistance to pathogenic microorganisms. Microbial infections may be prevented or reduced in swine populations by administration of immune lymphokines which have been produced by the splenic T cells of immunized swine. The process and compositions are particularly useful for the control of Salmonella in swine.

In accordance with this discovery, it is an object of this invention to provide a method to increase the resistance of swine to microbial infection by administering immune lymphokines thereto.

Another object of this invention is to provide a method for producing immune lymphokines which are effective for preventing or reducing the infection of swine by pathogenic microorganisms.

Yet another object of the invention is to provide compositions of immune lymphokines derived from the T cells of immunized swine which are effective for preventing or reducing the infection of swine by pathogenic microorganisms.

Other objects and advantages of this invention will become readily apparent from the ensuing description.

BRIEF DESCRIPTION OF THE DRAWINGS

FIG. 1. *Salmonella choleraesuis* Organ Invasion: Pigs were challenged with $1 \times 10^7$ CFU *Salmonella choleraesuis* (SC) orally on day 0. Organ invasion (liver, lung, spleen) data for SC infected control and SC infected PILK 3× groups are shown. Data represents the mean of 3 experiments ± SEM. Significant differences are indicated with an asterisk ($P<0.001$).

FIG. 2. Average Weight Gain: Pigs were weighed on day 0, day 7 (week 1), and day 14 (week 2). Total gain represents the sum of week 1 and week 2 gains for each group. Data for each group for each time point represent the mean of 3 experiments. A single asterisk represents a significant difference from all groups and a double asterisk indicates a significant difference from SC infected controls only ($P<0.001$).

FIG. 3. SC in Cecal Contents: Pigs were challenged with $1 \times 10^7$ CFU SC on day 0 orally. Data for SC infected controls and SC infected PILK 3× groups are shown. Significant differences are indicated with an asterisk ($P<0.05$).

DETAILED DESCRIPTION OF THE INVENTION

The method and immune lymphokine compositions of this invention are effective for protecting swine against infection by a wide variety of microorganisms. Without being limited thereto, the process and compositions are useful for providing protection against viral, bacterial, fungal, and protozoan swine pathogens, including those described in Wilcock and Schwartz (ibid) and The 1984 Yearbook of Agriculture: Animal Health [Hayes (ed.), U.S. Government Printing Office, LC 84-601135, 1984-451–784, pp. 277–306], the contents of each of which are incorporated by reference herein. In a preferred embodiment, the method and compositions are particularly effective for protecting swine against infection by Salmonella species such as *S. choleraesuis* and *S. typhimurium*. The invention may be practiced with any type of swine, including but not limited to pigs and hogs.

Immune lymphokines for use herein are derived from mature T lymphocytes (T cells) which have been recovered or isolated from swine. The invention may be practiced with T cells from any type of swine, although pigs and hogs are preferred sources. In any event, the swine selected as the source for the T cells should be immunologically competent or mature adults, having immune systems wherein the T cells may be effectively activated or stimulated in response to inoculation with an antigen of interest.

To produce the immune lymphokines, the swine are first immunized with an immunogen in vivo. The immunogen should be administered to the swine in an amount effective to activate or stimulate the T cells of that animal, that is, to induce cellular immunity mediated by T cells. The actual amount may be readily determined, and will vary with the immunogen, its formulation, the route and schedule of administration, and the subject animal. In a preferred embodiment, the immunogen is administered to the swine repeatedly (i.e. hyperimmunization), with at least one and most preferably two or three booster doses being administered after the initial inoculation, to produce T cells at a high activation state and effect maximal build-up of memory T cells specific for the target immunogen. While the immunization schedule is not critical, the doses are generally administered at approximately one week intervals. Inoculation of the animals may be made by various routes, although oral administration or injection are preferred. Optionally, the immunogen may be formulated with a pharmaceutically acceptable carrier to facilitate administration. The skilled practitioner will recognize that other routes of administration, immunization schedules, carriers or conventional adjuvants may be used.

The immunogens used to activate the T cells include but are not limited to immunogens of microorganisms pathogenic to swine, particularly viruses, bacteria, fungi, and protozoa. Preferred for use herein are immunogens of pathogens of swine, particularly Salmonella spp., such as *S. choleraesuis*, *S. typhimurium*, and *S. enteriditis*, and pathogenic *Escherichia coli*. The immunogen may also consist of, or be derived from, a target microorganism. In accordance with a preferred embodiment, the viable microorganism is used as the immunogen. However, the skilled practitioner will recognize that attenuated, killed, or inactivated microorganisms may be used as immunogens, as well as mutants or components or fragments thereof, as are conventional in the art. Suitable immunogens for use herein may be readily determined and include, for example, those described in Wilcock and Schwartz (ibid) or The 1984 Yearbook of Agriculture: Animal Health (ibid) for immunization of swine against a variety of pathogens.

Activated T lymphocytes may be recovered from the swine after the immunization. Generally, the cells will be harvested about one to three weeks, preferably two weeks, after the last immunization, to achieve a maximum activation state. However, the actual timing of the harvest will vary with the specific immunogen, the immunization dosage, and schedule. In accordance with the preferred embodiment, best results have ben obtained using mature T cells harvested from the spleen.

The recovered T cells may be used in pure or impure form. Although neither B-cells nor macrophages interfere with the process of this invention and appear to eventually die off, these and other cell types may nonetheless be removed to ensure purity of the T cells. Separation of the lymphocytes in general, or separation of the T cells in particular, from other cells may be performed using well known techniques, such as by density gradient centrifugation or absorption. In the preferred embodiment, splenic lymphocytes may be separated by contacting suspended cells with a plastic surface to remove adhering macrophages. T cells may be further separated from B-cells, for example, by affinity chromatography. In one embodiment, B-cells may be removed by absorption, for example, with nylon wool. The T cells may be readily eluted from the substrate while B-cells remain adhered.

Following their recovery from the immunized animal, the activated T cells are exposed in a culture media in vitro, to a mitogen in an amount effective to further stimulate or activate the cells to division or blastogenesis. During this culture, the immune lymphokines produced by the T cells are secreted into the culture medium and may be subsequently recovered therefrom. Techniques for in vitro lymphocyte activation which may be used herein are well known in the art, as are a variety of mitogens, and include those described by Weiler and Von Bulow (1987, Vet. Immunol. Immunopathol., 14:257–267) and Stites [Clinical Laboratory Methods for Detection of Cellular Immune Function, In: *Basic & Clinical Immunology*, fifth edition, Stites et al. (ed.), Lange Medical, Los Altos, Calif., (1984), pp. 362–365], the contents of each of which are incorporated by reference herein. Weiler and Von Bulow (ibid) also described the optimal conditions, including mitogen concentration, culture media, and environmental conditions for lymphokine production. Without being limited thereto, preferred mitogens for use herein include phytohemagglutinin (PHA), phorbol myristate acetate (PMA), and particularly concanavalin A (Con A).

In brief, the T cells are suspended in a suitable tissue culture medium with added mitogen and incubated, preferably at about 37° C. in a $CO_2$ containing atmosphere, for approximately 48 to 72 hours. The particular culture medium selected is not critical and a variety of tissue culture media may be used. However, without being limited thereto, culture is preferably conducted in serum-free RPMI medium. The amount of mitogen added to the media may be readily determined, and will vary with the particular mitogen selected and the cell concentration. As mentioned above, the immune lymphokines produced by the T cells will be secreted into the culture medium.

Following production, the immune lymphokines may be administered directly to the subject swine. Because the immune lymphokines are secreted, either a crude preparation of a culture of the T cells, or the culture supernatant free of cells and/or mitogen, may be recovered for subsequent use. Use of crude extracts or supernatants obviates the need for purification and is preferred. It is also understood that the immune lymphokines may be purified, such as by conventional chromatography or gel electrophoresis techniques. Optionally, the preparation containing the immune lymphokines may be further formulated with a conventional inert carrier to facilitate administration. For example, without being limited thereto, the immune lymphokines may be formulated with lactose or skim milk, or combined with a small amount of feed or water for use as a premix. Adjuvants conventional in the art for the treatment of swine, including those for the treatment of enteropathogens, may also be formulated with the immune lymphokines. Suitable adjuvants include but are not limited to vaccines, antitoxins, deworming agents, or selected antibiotics as described in The 1984 Yearbook of Agriculture (ibid). Non-therapeutic levels of antibiotics may also be administered to the swine as is conventional in the art.

Administration of the immune lymphokines may be at any time during the life of the animal. However, in the preferred embodiment, the lymphokines are administered to newborn swine or piglets at the time of or shortly after weaning, generally between about one to five weeks old, most typically between about three to five weeks old. The preparations of the immune lymphokines may be administered by any convenient route. In accordance with the preferred embodiment, we have unexpectedly discovered that the immune lymphokines may be administered orally, such as by oral gavage or by incorporation into the animals feed or water. Alternatively, the immune lymphokines may be administered by intraperitoneal (i.p.), subcutaneous, or intramuscular injection.

The immune lymphokines are administered in an amount effective to increase resistance of swine to infection by a target microorganism. An effective amount is defined herein as that amount which will significantly reduce or prevent the incidence of infection by a target microorganism in a treated swine in comparison to untreated control swine. A reduction of incidence of infection may be demonstrated by a significant reduction in the number of animals infected or the severity or pathogenicity of infection, in comparison with untreated control swine. It is also understood that when the target microorganism is a digestive system pathogen such as Salmonella species, a reduction of incidence of infection may be demonstrated by a significant inhibition of intestinal or cecal colonization by the microorganism (as indicated by one or more of reducing pathogen shedding, reducing the average pathogen concentration, or lowering the percentage of swine colonized) in comparison with untreated controls. Suitable amounts may be readily determined by the practitioner skilled in the art, and will vary with the age and size of the swine, and the target pathogen. Without being limited thereto, the preferred dosage is generally about 4–5 µg of substantially pure lymphokine per pound of body weight.

The following example is intended only to further illustrate the invention and is not intended to limit the scope of the invention which is defined by the claims.

EXAMPLE 1

Materials and Methods

Experimental Animals

Fourteen to 17 day-old piglets (Landrace X Yorkshire X Hampshire/Duroc) (average weight 13.5 pounds) were acquired from the Texas Department of Criminal Justice Ellis Unit Farrowing Farm (Huntsville, Tex.). Piglets were checked for general good health, ear-tagged, and randomly placed into pens in an isolation facility on the grounds of the USDA ARS FAPRL in College Station, Tex. Rectal swabs were obtained from all piglets upon arrival and were cultured for the presence of any Salmonella species [Andrews et al., Isolation and Identification of Salmonella, IN: *Bacteriological Analytical Manual*, 5th edition, Assoc. Official Analytical Chemists, Washington, D.C.]. Pens were equipped with nipple watering systems and feed was provided ad libitum using self-feeders. Additional warmth was provided by heating pads on the floor of each pen. For the first 7 days post-weaning, piglets were fed a Phase I diet (formulation provided by Dr. Knabe, Department of Animal Science, Texas A&M University) and for the last 7 days of the study were fed a Phase II diet (Dr. Knabe).

Bacteria

A porcine isolate of *Salmonella choleraesuis* (SC) var. Kunzendorf $_{102}$3246 obtained from the Veterinary Diagnostic Laboratory (Ames, Iowa—P. Fedorka-Cray). SC was selected for novobiocin-nalidixic acid (NONA) resistance in our laboratory and maintained in tryptic soy broth (TSB). Inocula for challenge with SC was prepared using sterile phosphate-buffered saline (PBS) and adjusted to a stock concentration of $10^9$ colony forming units (CFUs) per milliliter using a spectrophotometer with a 625 nm reference wavelength. The viable cell concentration of the inocula was determined by colony counts on brilliant green agar (BGA) with NONA (Difco Laboratories, Detroit, Mich.). The $10^9$ stock of SC was serially diluted to $1\times10^7$ CFU/ml using PBS.

Porcine *Salmonella enteritidis*-immune Lymphokine Preparation

Two guilts (Landrace x Yorkshire) weighing approximately 180 pounds each, obtained from the TDCJ and determined to be Salmonella species-free were used for immune lymphokine (PILK) production. Pigs were fed a nonmedicated finisher diet ad libitum. Pigs were challenged three times weekly for four weeks with 10 ml of $10^9$ CFU *Salmonella enteritidis* (SE). Five ml of SE were given by oral gavage and 5 ml were given intranasally. During the fifth week pigs were not challenged with SE, and at the end of the fifth week pigs were euthanized and spleens were obtained aseptically. Splenic T cells were isolated as previously described (Tellez et al., 1993, Avian Dis., 37:1062–1070). T cells were placed in 175 cm² T flasks at a concentration of $5 \times 10^6$ cells/ml in serum-free RPMI 1640 (Sigma) with 7.5 µl of concanavalin A (Con A) and incubated for 48 hours at 37° C. in a 5% $CO_2$ incubator. After incubation, supernatants were collected and centrifuged at 2000×g for 15 minutes to remove all cells. Supernatants were treated with α-mannopyrannoside to inactivate any residual Con A and concentrated five-fold using YM-100 and YM-10 membranes (Amicon Corp.). The retentate was then sterile fltered using 0.22 µm filters (Corning) and stored at −20° C.

Experimental Design

Pigs were randomly assigned to one of five groups: Group (1)=noninfected controls (n=7), Group (2)=noninfected PILK 3× (n=7), Group (3)=SC infected controls (n=10), Group (4)=SC infected PILK 1× (n=10), Group (5)=SC infected PILK 3× (n=10). Pigs were acclimated to their surroundings for three days prior to the study. During the acclimation period, rectal swabs were taken from individual pigs to determine the presence of any Salmonella species and all piglets were determined to be free of any Salmonella species. On day 0, pigs were weighed and administered respective treatments. Pigs in groups 2, 4, and 5 were administered 5 ml of PILK by oral gavage (approximately 60 µg/pig or 4–5 µg/pound of body weight). Pigs in groups 1 and 3 were administered 5 ml of RPMI 1640 via oral gavage. One hour post-administration, pigs in groups 3, 4, and 5 were challenged with $1 \times 10^7$ CFU SC by oral gavage. Daily rectal swabs from individual pigs in groups 3, 4, and 5 were obtained and weights for all groups were recorded on days 7 and 14. Pigs in Groups 2 and 5 were administered PILK twice more, on days 5 and 10 for a total of 3 PILK treatments (3×). Pigs in groups 1, 3, and 4 received RPMI 1640 on these days. On day 14, pigs in groups 3, 4, and 5 were euthanized, weighed, and tissue samples were aseptically collected. Tissue samples from the tonsil, liver, lung, spleen, ileocolic lymph nodes, ileocolic junction, and cecal contents were cultured for the presence of SC using previously described methods (Kogut et al., 1996, Avian Pathol., 25:737–749). Briefly, samples were inoculated into GN Hajna broth (Difco Laboratories, Detroit, Mich.) for 24 hr at 37° C.; 100µl of GN Hajna broth was then placed into Rappaport-Vassiliadas (RV) (Difco Laboratories) broth for 24 hr at 37° C. RV broth was then streaked onto BGA NONA plates using sterile inoculation loops and incubated at 37° C. for 24 hr. Plates were scored positive or negative for the presence of SC. Random colonies from BGA NONA plates were tested using SC antisera. Three repetitions of this experiment were performed.

Statistics

Statistical analysis was performed using Sigma Stat software (Jandel Scientific, San Rafael, Calif.). Differences between groups were analyzed using the paired t test. All analysis were performed using pooled data from three replicates of this experiment.

Results

Organ Invasion by SC

In FIG. 1, results are presented as the mean percentage of three replicate experiments to determine the effects of PILK on SC organ invasion in weaned pigs. The PILK 3× group had a highly significant (P<0.001) reduction in the number of pigs in which SC was recovered from the liver, lung, and spleen. The PILK 1× infected group had a biological reduction in organ invasion, but not a statistical reduction. Culture of lymphoid tissue, including tonsil, ileocolic junction, and ileocolic lymph nodes for the presence of SC did not reveal any differences between any of the infected groups; all SC infected groups had high levels (80–90%) of positive lymph tissue.

Weight Gain

Pigs in the SC infected PILK 3× group gained weight comparable to pigs in the noninfected control group (FIG. 2). Pigs in the PILK 3× noninfected group gained a significant amount more than even the noninfected control group (P<0.01) and the SC infected control group (P<0.001). No statistical differences were noted between the PILK 1× infected group and infected control pigs.

SC Recovered From Cecal Contents

There was a highly significant reduction in the number of pigs positive for SC in cecal contents in the PILK 3× group (P<0.001). Only 13% of pigs in the PILK 3× infected group had SC recovered from the cecal contents while the SC infected control group had over 55% of pigs positive for SC in the cecal contents. The PILK 1× group was not statistically different from the SC infected control pigs in the isolation of SC from cecal contents.

DISCUSSION

The purpose of these experiments was to determine if lymphokines (PILK) obtained from the T cells of SE-immune pigs would protect weaned piglets from SC organ invasion and cecal colonization and whether this protection would translate into higher weight gains even in the presence of an infection with SC. Results presented here indicate that PILK given multiple times reduces SC organ invasion significantly (P<0.001), significantly decreases SC cecal colonization (P<0.001), and improved weight gain by pigs in the presence of an SC infection.

Susceptibility to infectious diseases at weaning may be attributed to several factors, including loss of maternally derived antibodies, developmental deficiencies in the immune response, and elevated glucocorticoid levels in animals during weaning. Production pressures on the swine industry force producers to look for ways to increase production. One possible means to attain increased production would be to wean piglets from sows earlier. However, weaning pigs and other species at an early age has been shown to have deleterious effects on the health and survivability of these animals, most likely due to a deficient immune response and subsequent inability to fight off infections [Blecha et al., 1983, (ibid); Wilcock and Schwartz (ibid); El-Awar and Hahn (ibid); Carter and Martens (ibid); Drieson et al. (ibid); Selim et al. (ibid); Shi et al., J. Leuk. Biol., 1994, 56:88–94; and Hoskinson et al., J. Anim. Sci., 1990, 68:2471–2478]. If loss of maternal antibodies and developmental deficiencies in the immune response of young pigs are at least partially responsible for the increased susceptibility to bacterial disease observed at weaning, early weaning of pigs leaves these animals at an even greater defensive disadvantage, immunologically speaking, than pigs weaned at older ages.

Salmonella species in swine production are a major concern to producers and consumers of pork products. We have demonstrated that a product derived from the T cells of SE-immune swine, when administered prophylactically to weaned piglets, protects these pigs from *Salmonella choleraesuis* infection, causing reductions in SC organ invasion and SC in the cecum, and improves weight gain in the presence or absence of a SC infection.

It is understood that the foregoing detailed description is given merely by way of illustration and that modifications and variations may be made therein without departing from the spirit and scope of the invention.

We claim:

1. A method for increasing the resistance of a subject swine to infection by a pathogenic microorganism comprising orally administering to said subject swine a composition comprising impure immune lymphokines in an amount effective to reduce the incidence of infection by said pathogenic microorganism, wherein said immune lymphokines have been obtained from the T cells of a donor swine which has been immunized with an immunogen in an amount effective to stimulate or activate said T cells.

2. The method of claim 1 wherein said immune lymphokines have been obtained by the process comprising (a) providing T cells recovered from a donor swine which has been immunized in vivo with an immunogen of a microorganism pathogenic to said donor swine, said immunogen being effective to stimulate or activate T cells in said donor swine;

(b) culturing said T cells in a culture medium containing said mitogen effective for secondary stimulation of said T cells; and (c) recovering said immune lymphokines produced by said T cells.

3. The method as described in claim 1 wherein said subject swine are selected from the group consisting of domestic pigs and hogs.

4. The method as described in claim 1 wherein said composition comprising immune lymphokines is administered to said subject swine between about one to five weeks old.

5. The method as described in claim 1 wherein said composition further comprises a carrier.

6. The method as described in claim 1 wherein the step of administering comprises providing said composition in combination with feed for said subject swine.

7. The method as described in claim 1 wherein the step of administering comprises providing said composition in combination with water for said subject swine.

8. The method as described in claim 1 wherein said immunogen is a bacterial immunogen.

9. The method as described in claim 1 wherein said immunogen comprises a Salmonella species.

10. The method as described in claim 1 wherein said mitogen is selected from the group consisting of Concanavalin A, phytohemagglutinin, and phorbol myristate acetate.

11. The method as described in claim 1 wherein said T cells are splenic T cells.

* * * * *